United States Patent
Duff et al.

(10) Patent No.: US 6,713,253 B1
(45) Date of Patent: Mar. 30, 2004

(54) DETECTING GENETIC PREDISPOSITION TO SIGHT-THREATENING DIABETIC RETINOPATHY

(75) Inventors: Gordon W. Duff, South Yorkshire (GB); Patrick R. S. Richardson, Litton Nr. Buxton (GB); Ian G. Rennie, Newbold (GB)

(73) Assignee: Interleukin Genetics, Inc., Waltham, MA (US)

( * ) Notice: Subject to any disclaimer, the term of this patent is extended or adjusted under 35 U.S.C. 154(b) by 0 days.

(21) Appl. No.: 09/037,472

(22) PCT Filed: Oct. 9, 1997

(86) PCT No.: PCT/GB97/02790

§ 371 (c)(1),
(2), (4) Date: Mar. 10, 1998

(87) PCT Pub. No.: WO98/15653

PCT Pub. Date: Apr. 16, 1998

(30) Foreign Application Priority Data

Oct. 10, 1996 (GB) .............................. 9621129

(51) Int. Cl.⁷ .......................... C12Q 1/68; C12P 19/34; C07H 21/04; C07H 21/02
(52) U.S. Cl. ........................ 435/6; 435/91.2; 536/23.5; 536/24.31; 536/24.33
(58) Field of Search .......................... 435/6, 91.2, 810; 536/23.5, 24.31, 24.33

(56) References Cited

U.S. PATENT DOCUMENTS

| | | | |
|---|---|---|---|
| 5,039,606 A | 8/1991 | Nepon | 435/6 |
| 5,196,308 A | 3/1993 | Nepom et al. | 435/7.21 |
| 5,686,246 A | 11/1997 | Kornman et al. | 435/6 |
| 5,698,399 A | 12/1997 | Duff et al. | 435/6 |

OTHER PUBLICATIONS

Adamis, et al. "Increased Vascular . . . " *Am. J. Opthmal.* 118(4): 445 (Oct. 1994).
Aiello, et al., "Vascular Endothelial Growth . . . " *N.E.J.M.* 331(22): 1480 (Dec. 1994).
Blakemore, et al., *Hum. Genet.* 97(3): 369–74 (1996).
Blakemore, et al., *Arthritis Rheum.* 37: 1380–85 (1994).
Center for Disease Control an Prevention, the, "National Diabetes Fact Sheet" (Nov. 1995).
Clark, et al., *Nuc. Acids Res.* 14: 7897 (1986); Erratum in *Nuc. Acids Res.* 15(2): 868 (1987).
Clay et al., "Interleukin–1 receptor antagonist gene polymorphism association with lichen scleroses", *Hum. Genet.* 94: 407–410 (1994).
Clay et al., "Novel interleukin–1 receptor antagonist exon polymorphisms and their use allele–specific mRNA assessment", *Human Genetics* 97(6): 723–726 (Jun. 1996).
Cork, et al., *J. Invest. Dermatol.* 104(5 Supp.): 15S–16S (1995).
di Giovine et al., "Single base polymorphism at –511 in the human interleukin–1β gene (IL1β)", *Human Molecular Genetics* 1(6):;410 Abstract only (1992).
Dinarello, "Interleukin–1 and Interleukin–1 Antagonism" *Blood* 77: 1627 (1991).
DRS Report No. 7 "A Modification of the . . . " *Invest. Opthalmol. Vis. Sci.* 21: 210 (1981).
DRS Report No. 8 "Photocoagulation Treatment of . . . " *Pthalmol.* 88(7): 583 (1981).
Duff, "Cytokines and Anti–Cytokines" *Br. J. Rheumatol.* 31(Supp. 1): 15 (1993).
Duff, "Molecular Genetics of Cytokines", The Cytokine Handbook (1994) 2nd ed., Chap. 2: 21–30.
ETDRS No. 1, "Photocoagulation for diabetic Macula Edema" *Arch. Opthamol.* 103: 1796 (1993).
ETDRS No. 9, "Early Coagulation . . . " *Opthalmol.* 98: 766 (1991).
ETDRS No. 12, "Fundus Photographic Risk . . . " *Opthalmol.* 98: 823 (1991).
Franks, et al . . . "Cytokines in Human . . . " *Current Eye Res.* 11(Supp.): 187 (1992).
Furutani et al., "Complete Nucleotide Sequence" *Nuc. Acids Res.* 14: 3167 (1992).
Hu, et al., "Inhibition of Aniogenesis . . . " *Inflammation* 18(1): 45 (1994).
Hu & Fan "Protein Kinase C Inhibitor . . . " *Inflammation* 19(1): 39 (1995).
Klein et al., "Self–Rates Health and Diabetes of Long Duration," *Diabetes Care*, 21(2): 236–240 (Feb. 1998).
Ko et al., "An (A–C)ₙ Dinucleotide Repeat Polymorphic Marker at the 5' End of the Aldose Reductase Gene is Associated With Early–Onset Diabetic Retinopathy in NIDDM Patients," *Diabetes* 44:727–732 (1995).
Mansfield et al., "Novel Genetic Association Between Ulcerative Colitis and the Anti–Inflammatory Cytokine Interleukin–1 Receptor Antagonist", *Gastroenterology* 106: 637–642 (Mar. 1994).
McCarren, "Genetics of Diabetes", Publication American Diabetes Association, 1994.
Murata, et al., "Vascular Endothelial Growth . . . " *Opthalmic Res.* 27(1): 48 (1995).

(List continued on next page.)

*Primary Examiner*—Carla J. Myers
(74) *Attorney, Agent, or Firm*—Ivor E. Elrifi; Mintz, Levin, Cohn, Ferris, Glovsky and Popeo, P.C.

(57) ABSTRACT

A method and kit for predicting increased risk of sight-threatening diabetic retinopathy which includes isolating genomic DNA from a sample from a diabetic patient. The genetic polymorphism pattern for the genes IL-1A, IL-1B and IL-1RN is then identified in the DNA. The identified pattern is compared with control patterns of known polymorphisms, and patients expressing a genetic polymorphism pattern associated with increased risk of sight-threatening diabetic retinopathy are identified.

5 Claims, 2 Drawing Sheets

OTHER PUBLICATIONS

Nedospasov, et al., "Tandem Arrangement of Genes . . . " *Cold Spring Harbor Sympos. Quant. Biol.* 60: 611 (1986).

Nicklin, et al., *Genomics* 19: 382–4 (1994).

Pe'er, et al., "Hypoxia–Induced Expression of . . . " *Lab. Invest.* 72(6): 638 (Jun. 1995).

Pfeiffer, et al., "Vascular Endothelial Growth . . . " *Dtsch. Med. Wochenschr.* 120(42): 1453 (Oct. 1995).

Pociot, et al., *Eur. J. Clin. Invest.* 22: 396–402 (1992).

Richardson, et al., *Invest. Opthalmol.* 38(4): 3714 (1997).

Seaquist, et al., "Familial Clustering of . . . " *N.E.J.M.* 320: 1161 (1989).

Tarlow, et al., *J. Invest. Dermatol.* 103: 387 (1994).

Todd, "Genetic Control of . . . " Immulol. *Today* 11:122 (1990).

Verjans, et al., "Polymorphism of the TNF Region in . . . " *Rheum. Dis. Clin. North Am.* 18: 177 (1992).

Woolf, "Estimating the Relationship between Blood Groups & Disease" *Annals Human Genet.* 19: 251 (1955).

FIG.1

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "PRIMER"

(xi) SEQUENCE DESCRIPTION: SEQ ID NO:1:

AAGCTTGTTC TACCACCTGA ACTAGGC                  27

```
(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:2:

GTACCTTCCG AGTATACATT                                                      20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

TGGCATTGAT CTGGTTCATC                                                      20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

GTTTAGGAAT CTTCCCACTT                                                      20

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

CTCAGCAACA CTCCTAT                                                         17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

TCCTGGTCTG CAGGTAA                                                         17
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:7:

TGTTCTACCA CCTGAACTAG GC          22

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:8:

TTACATATGA GCCTTCCATG          20

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:9:

AAGCTTGTTC TACCACCTGA ACTAGGC          27

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:10:

TTACATATGA GCCTTCCATG          20

DETECTING GENETIC PREDISPOSITION TO SIGHT-THREATENING DIABETIC RETINOPATHY

This application is the national phase of PCT Patent Application GB97/02790 filed on Oct. 9, 1997; which claims priority to UK Provisional Application No. GB 9621129.7, filed on Oct. 10, 1996.

BACKGROUND OF THE INVENTION

1. Technical Field of the Invention

This invention relates to a method of detecting a predisposition to, and determining risk of, sight-threatening diabetic retinopathy. The invention also provides diagnostic kits for the assessment of risk of developing sight-threatening diabetic retinopathy.

2. Description of the Prior Art

Insulin dependent (Type I) and non-insulin dependent (Type II) diabetes mellitus are distinct diseases and patients with either form of the disease are at risk of developing microvascular and macrovascular complications such as neuropathy, nephropathy, retinopathy, atherosclerosis and cardiovascular disease. These complications are a major clinical burden in diabetes, but their pathogenesis is not well understood. Susceptibility to diabetic complications has been reported to be inherited independently of diabetes itself. [Seaquist et al., 1989; Ko et al., 1995].

In the United States there are approximately 16 million diabetics, of which it is estimated that only half are diagnosed [CDC, 1995]. Retinal disease (retinopathy) is one of several complications of diabetes and is primarily the result of disruption of small blood vessels, such as capillary leakage, destruction or occlusion of capillaries leading to ischemia, and the uncontrolled growth of new vessels. In many situations, these changes affect the macula, which is the area of the retina that is specialized to color and visual acuity. All of these are consequences of retinal capillary closure or leakage and are not thought of as retinal inflammation.

Characteristic anatomical and physiological changes occur in the retinal circulation. Clinically, they may be classified as background changes, maculopathy and proliferative disease. Any may be present at any level of retinopathy in the same patient, but not all cause visual loss.

Sight-threatening diabetic retinopathy is one of the most common complications of diabetes and is the most common cause of vision loss in the under 65 years age group in developed countries, as a result of non-resolving vitreous hemorrhage, traction retinal detachment or diabetic maculopathy. Sight-threatening diabetic retinopathy refers to diabetic complications affecting the retina that predictably lead to severe loss of vision. These changes include non-resolving vitreous hemorrhage, tractional retinal detachment, or retinal edema.

The following is a description of characteristic anatomical and physiological changes which occur in the retinal circulation in diabetes.

Background Diabetic Retinopathy (BDR)

Microaneurysms and intra-retinal microvascular abnormalities (IRMA) are found adjacent to areas of retinal capillary non-perfusion. Infarcts of the nerve fiber layer (sometimes called cotton-wool spots) and intra-retinal hemorrhages are also included in BDR, as are any areas where fluid swells the retina (retinal edema) which does NOT threaten the central vision. Background retinopathy is not associated with visual loss and does not therefore require treatment.

Maculopathy, Including Clinically-significant Macular Edema (CSME)

The macula lies at the posterior pole of the retina and is specialized for color and accurate vision (high visual acuity) at the fovea which lies centrally in the macula. It may be altered structurally by fluid or lipids collecting in the retina from localized for widespread leaking retinal capillaries (focal or diffuse maculopathy respectively) or by non-perfusion of para-foveal capillaries (ischemic maculopathy). Additionally, retinal traction, macular hemorrhage or macular hole formation will reduce visual acuity.

Proliferation Diabetic Retinopathy (PDR)

As areas of capillary non-perfusion enlarge new vessels arise from the venous circulation at the optic disc (NVD: new vessels at the disc) or from branch retinal veins (NVE: new vessels elsewhere).

Prior to the formation of frank new vessels, there is a pre-proliferative stage which is recognized clinically, as indicated by dilated, beaded retinal veins and signs of widespread retinal non-perfusion. Once the pre-proliferative stage has been identified, the risk of developing PDR in one year is 52% and of developing 'high-risk, PDR in five years is 60% (ETDRS12, 1991).

High-risk proliferative diabetic retinopathy is a characteristic appearance of the retina in which 50% of the patients will develop severe visual loss within 5 years. Severe visual loss is a fall of 3 or more lines of visual acuity on the eye chart on two separate occasions 3 months apart. The characteristic retinal findings that would qualify for the diagnosis of high-risk PDR include one or more of the following:

1. New vessels at the disc (NVD) that involve at least ¼ to ⅓ of the disc area. This is diagnosed by comparison to Standard Photograph 10A of the Modified Airlee House Classification of Diabetic Retinopathy [DRS Report No. 7, 1981];
2. NVD less than ¼ of the disc area if fresh vitreous hemorrhage is present; and
3. New vessels elsewhere (NVE) greater than or equal to ½ the disc area in size if fresh vitreous hemorrhage is present.

Appropriately timed laser treatment can reduce the two year incidence of severe visual loss (SVL) in 'high-risk, proliferative disease by 50% and the incidence of moderate visual loss (MVL) over two years in those with macular edema by 50%. [DRS8, 1981; ETDRS1, 1985; ETDRS9, 1991].

Advanced Diabetic Retinopathy

Initially, these new vessels leak and are fragile, with the resulting vitreous hemorrhage causing a sudden, often profound, loss of vision. The blood may resolve over the following weeks, but it may become organized into a dense opaque mass in the vitreous which does not resolve.

Fibrous tissue appears adjacent to these new vessels, which subsequently contracts, leading to tractional retinal detachments. New vessels may also grow across the iris and prevent fluid draining from the eye, causing rubeotic glaucoma.

Epidemiology

Approximately 16 million people in the United States have diabetes mellitus, of which 50% are diagnosed. Of these, 10–15% have insulin-dependent diabetes mellitus (Type I; IDDM) which is usually diagnosed before the age of 40 years of age. The majority have non-insulin dependent diabetes (Type II DM; NIDDM), some of which may be treated with insulin. From the Wisconsin epidemiological study of diabetic retinopathy, duration of diabetes is associated with increasing incidence of diabetic retinopathy [Klein et al, 1994]. Other risk factors include age less than 30 at diagnosis, being male, raised glycosylated hemoglobin ($HbA_{1c}$), hypertension, hyperlipidemia, pregnancy and diabetic nephropathy.

Genetic testing is now possible (see U.S. Pat. Nos. 4,582,788 and 5,110,920) for diseases associated with, or caused by, one to two genes, once the genes are identified, to determine the risk of a person carrying a given gene for the disease (see for example U.S. Pat. Nos. 4,623,619, 4,801,531, 4,666,828 and 5,268,267).

U.S. Pat. Nos. 5,039,606 and 5,196,308, as well as Pociot et al. (1992) disclose methods of identifying people who are at risk for developing diabetes. However, these references do not provide methods of determining among diabetics those who are at risk for developing sight-threatening retinopathy. Ko et at. (1995) do provide a single factor, a polymorphic marker at the 5' end of the aldose reductase gene, that is associated with early onset of diabetic retinopathy in Chinese patients with NIDDM. However, this provides only one marker, which as shown in the Ko et al. reference does not identify all persons at risk. Additionally, the population studied is not the same ethnic population as found in the United States and much of Europe, therefore the data may not be completely applicable to US and European populations.

The pathogenesis of retinal complications from diabetes is not well understood. Michelson (1940) however, proposed that as diabetes produces destruction of blood vessels in the retina, localized areas of ischemia develop resulting in the release vasoproliferative factors. Research in recent years has focused on growth factors that stimulate vascular proliferation, especially basic fibroblast growth factor (BFGF) and vascular endothelial growth factor (VEGF) which are modulated by hypoxia. [Adamis et al., 1994; Aiello et al., 1994; Koyama et al., 1994; Lowe et al., 1995; Malecaze et al., 1994; Mansfield et al., 1994; Murata et al., 1995; Peler etal., 1995; Pfeiffer, 1995; Pfeiffer and Schatz, 1995].

Genetic testing (also called genetic screening or genotyping) can be defined broadly as the testing of nucleic acid of a patient in an analytical capacity to determine if a patient contains mutations (or alleles or polymorphism) that either cause or increase susceptibility to a disease state or are in "linkage disequilibrium" with the gene causing a disease state.

Linkage disequilibrium refers to the tendency of specific alleles to occur together more frequently than would be expected by chance. Alleles at given loci are in equilibrium if the frequency of any particular set of alleles (or haplotype) is the product of their individual population frequencies. The cause of disequilibrium is often unclear. It can be due to selection for certain allele combinations, or to a recent admixture of genetically heterogeneous populations. In addition, in the case of markers that very tightly link to a disease gene, an association of an allele (or a group of linked alleles) with the disease gene is expected if the disease mutation occurred in the recent past, so that sufficient time has not elapsed for equilibrium to be achieved through recombination events in that small chromosomal region.

The early detection of a predisposition to genetic diseases presents the best opportunity for medical intervention. Early genetic identification of risk may improve the prognosis for a patient through supervision and early intervention before the clinically detectable disorder occurs.

In cases where patients with similar symptoms are treated with variable success, sophisticated genetic testing can differentiate individual patients with subtle or undetectable differences and can lead to more suitable individual treatments. Early intervention may involve methods such as gene therapy or treatment with IL-1 modulators. With the development of genetic testing, it is now possible to identify gene mutations that indicate a propensity to develop disease, even when the disease is of polygenic origin. The number of diseases that can be identified by molecular biological methods continues to grow with increased understanding of the genetic basis of multifactorial disorders (see, e.g., U.S. Pat. Nos. 4,582,788; 5,110,920; 4,801,531; 4,666,828; and 5,268,267).

The IL-1 gene cluster is located on the long arm of human chromosome 2 (2q13) and contains at least the genes for IL-1α (IL1A), IL-1β (IL1B), and the IL-1 receptor antagonist (IL1RN) within a region of 430 Kb (Nicklin, et al., *Genomics* 19: 382–4 (1994)). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and the hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Certain alleles from the IL-1 gene cluster are known to be associated with particular disease states. For example, IL1RN allele 2 is associated with coronary artery disease, osteoporosis, nephropathy in diabetes mellitus (Blakemore, et al., *Hum. Genet.* 97(3): 369–74 (1996)), alopecia areata (Cork et al., *J. Invest. Dennatol.* 104(5 Supp.): 15S–16S (1995)), Graves disease (Blakemore, et al., *J. Clin. Endocrinol.* 80(1): 111–5 (1995)), systemic lupus erythematosus (Blakemore, et al., *Arthritis Rheum.* 37: 1380–85 (1994)), lichen sclerosus (Clay, et al., *Hum. Genet.* 94: 407–10 (1994)), and ulcerative colitis (Mansfield, et al., *Gastoenterol* 106(3): 637–42 (1994)). The IL1B(TaqI) allele 2 from marker+3953 of IL1B is also associated with psoriasis and insulin dependent diabetes in DR3/4 patients (di Giovine, et al., Cytokine 7: 606 (1995); Pociot, et al., *Eur J. Clin. Invest.* 22: 396–402 (1992)), and severe periodontal disease (kornman, et al. *J. Chin. Periodon.* 24:72 (1997)).

IL-1 has been shown to play a role in the pathogenesis of Type I diabetes (Dinarello, 1991; Todd, 1990, Mandrup-Poulsen et al., 1993). There is no reported evidence to support a role for IL-1 in either proliferative diabetic retinopathy or maculopathy.

There has been a report on the purported role of cytokines in angiogenesis (Hu and Fan, 1995; Hu et al., 1994). However, Franks et al. [1992]) investigated IL-1, IL-6, IL-2 and TNF in vitreous and aqueous aspirates from eyes undergoing vitrectomy for the treatment of various eye diseases. IL-6 was observed in 6 samples from eyes with diabetic retinopathy (range=5 to 480 pg/ml). Although IL-1 was detected in 80% of all the samples investigated, concentrations of this cytokine greater than 3pg/ml were only observed in one specimens from eyes with uveitis (5 and 20 pg/ml, respectively) and two samples from eyes with diabetic retinopathy (3 and 31 pg/ml, respectively). TNF was present in 1 sample from eyes with diabetic retinopathy (4 pg/ml), and IL-2 was detected in 2 samples from eyes with diabetic retinopathy. The authors concluded that the cytokine presence indicated that a local inflammatory processes may be switched on during many eye diseases and may amplify the clinical signs. The authors did not suggest and their data does not show any primary role for cytokines in the clinical severity of retinopathy. These authors have not reported any follow-up to this observation, and literature searches revealed no other studies that examined cytokines in diabetic retinopathy. The focus in the literature has therefore remained that the dominant factor in controlling clinical outcome is mediated by glucose metabolic factors.

Genetic variation at the multiple loci controlling immune responses, particularly cytokines, has been a factor in determining susceptibility to diseases with inflammatory components. However, diabetic retinopathy is not an inflammatory condition. As discussed above given the tissue changes seen in retinopathy some local production of cytokines can be expected as was seen by Franks et al. [1992], but this is not an inflammatory condition.

It was therefore unexpected to find for a condition that is not primarily inflammatory in nature, both clinically-significant macular edema (maculopathy; CSME) and proliferative diabetic retinopathy (PDR), associated with cytokine gene polymorphisms. The use of combinations of different cytokine polymorphisms indicates those patients who require closer observation and a more aggressive approach to retinopathy when it occurs.

Therefore, it was an objective of the present invention to determine genetic predictors for the risk of developing sight-threatening diabetic retinopathy. It would be useful to identify the genotypes and thereby identify diabetic patients who are susceptible to sight-threatening retinopathy so that early and aggressive monitoring and therapy can be initiated. Further, those patients who may be at higher risk by having the risk factor set forth in the Ko et al. paper and an additional predisposition based on the present invention need to be identified.

SUMMARY OF THE INVENTION

According to the present invention, a method for predicting risk of sight-threatening diabetic retinopathy is disclosed. The method includes the steps of isolating DNA from a patient and determining the DNA polymorphism pattern of the genes that code for IL-1α, IL-1β and IL-1ra. The identified pattern from patients may be compared with controls of known DNA polymorphism patterns thereby identifying patients carrying a genetic polymorphism pattern associated with increased risk of sight-threatening diabetic retinopathy. Patients so identified can then be treated more aggressively in the early stages of diabetes to reduce or prevent the occurrence of severe retinopathy which leads to loss of sight.

The present invention further discloses a kit for the identification of a patient's genetic polymorphism pattern associated with increased risk of developing sight-threatening diabetic retinopathy. The kit includes DNA sample collecting means and means for determining a genetic polymorphism pattern. The kit may also comprise control samples or standards so that a patient's risk of sight-threatening diabetic retinopathy can be determined.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

According to the present invention, diabetic patients without overt retinopathy are identified as having a genetic predisposition for sight-threatening retinopathy by detecting the presence of specific DNA polymorphisms in the gene sequences that code for IL-1α, IL-1β and IL-1rα as set forth herein below.

A "retinopathy" is defined generally as any disease of the retina. Briefly, diabetic retinopathy is one of the most common complications of diabetes as a result of non-resolving vitreous hemorrhage, traction retinal detachment or diabetic maculopathy. All of these are consequences of retinal capillary closure or leakage. "Sight-threatening diabetic retinopathy" refers to diabetic complications affecting the retina that predictably lead to severe loss of vision. Retinal disease is one of several complications of diabetes and is primarily the result of disruption of small blood vessels and the uncontrolled growth of new vessels. In some situations, these changes affect the macula, which is the area of the retina that is specialized to color and visual acuity.

The term "marker," as used herein, refers to a specific site in the genome which exhibits sequence variations between individuals. For example, herein described is a marker for identification of propensity to develop sight-threatening diabetic retinopathy.

The term "allele" refers to the different sequence variants found at given markers. The sequence variants may be single or multiple base changes, including insertions, deletions or substitutions or may be variable number of sequence repeats and the like.

The term "linkage disequilibrium" refers to the co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in 'linkage equilibrium.'

The term "haplotype" is a set of alleles that are inherited together as a group (are in linkage disequilibrium). As used herein, haplotype is defined to include those haplotypes that occur at statistically significant levels ($p_{corr} \leq 0.05$). As used herein the phrase "an IL-1 haplotype" refers to a haplotype in the IL-1 loci.

As used herein, the process of "detecting alleles" is variously described as "genotyping, determining or identifying an allele or polymorphism," or any similar phrase. The allele actually detected might be a disease-causing mutation, or a mutation that is in linkage disequilibrium with a disease-causing mutation. It will be manifest in the genomic DNA of a patient, but may also be detectable from RNA or protein sequences transcribed or translated from this region.

By "propensity," "predisposition" or "susceptibility" for disease what is meant is that certain alleles are hereby discovered to be "associated" with sight-threatening diabetic retinopathy. They are thus over represented in frequency in individuals with disease as compared to healthy individuals.

The term "polymorphism" as used herein refers to variation in the gene sequence. The polymorphisms can be those variations (DNA sequence differences) which are generally found between individuals or different ethnic groups and geographic locations which, while having a different sequence, produce functionally equivalent gene products. The term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Further, the term is also used interchangeably with allele as appropriate.

The invention is directed to a method of predicting the propensity or predisposition of a patient to sight-threatening diabetic retinopathy by genotyping the patient's DNA at an IL gene cluster. The patient's genotype may be compared with a control sample that contains one or more alleles from an IL haplotype, such as but not limited to the IL-1A, IL-1B and/or IL-1RN marker DNA is extracted from a suitable specimen using techniques known to those skilled in the art. Suitable specimens are those which comprise DNA and include, but are not limited to blood, buccal swabs and saliva.

In a preferred embodiment, the DNA will be obtained from blood cells collected from a finger prick of the patient with the blood collected on absorbent paper. In a further preferred embodiment, the blood will be collected on an AmpliCard™ (University of Sheffield, Section of Molecular Medicine, Royal Hallamshire Hospital, Sheffield, England S10 2JF). The DNA is then isolated from the dried blood spots and then target sequences amplified using appropriate techniques.

Techniques for determining the presence or absence of the particular allele of interest may be nucleic acid techniques based on size or sequence, such as restriction fragment length polymorphism (RFLP), nucleic acid sequencing, or hybridization. These techniques may also comprise the step of amplifying the nucleic acid before analysis. Amplification techniques are known to those of skill in the art and include cloning, polymerase chain reaction (PCR), polymerase chain reaction of specific alleles (PASA), ligase chain reaction, nested polymerase chain reaction, and the like. Amplification products may be assayed in a variety of ways, including size analysis, restriction digestion followed by size analysis, detecting specific tagged oligonucleotide primers in the reaction products, allele-specific oligonucleotide (ASO) hybridization, sequencing, hybridization, and the like.

PCR based detection means include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be detected. Other techniques are known in the art to allow multiplex analyses of a plurality of markers.

The amplified DNA sequences from the template DNA are then analyzed using restriction enzymes to determine the genetic polymorphism present in the amplified sequences and thereby provide a genetic polymorphism profile of the patient. Allele detection techniques may be protein based if a particular allele produces a protein with an amino acid variant. For example, epitopes specific for the amino acid variant can be detected with monoclonal antibodies. Likewise, it is possible to detect alleles if they are present in processed RNA by techniques that are known in the art.

Another embodiment of the invention is directed to kits for detecting a propensity for enhanced risk of sight-threatening diabetic retinopathy in a patient. The kits can be used pre- or post-symptomatically or prenatally. The kit may comprise one or more oligonucleotide capable of hybridizing to nucleic acid from the IL gene cluster. A number of assay formats are useful for genotyping using the provided oligonucleotide. The most common formats involve nucleic acid binding, such binding to filters, beads, or microtiter plates and the like. Techniques may include dot blots, RNA blots, DNA blots, PCR, RFLP, and the like.

The oligonucleotide may be a variety of natural and synthetic compositions such as synthetic oligonucleotide, restriction fragments, cDNAs, synthetic PNAs, and the like. The assay may also employ labeled oligonucleotide to allow ease of identification in the assays. Examples of labels which may be employed include radiolabels, enzymes, fluorescent compounds, streptavidin, avidin, biotin, magnetic moieties, metal binding moieties, antigen or antibody moieties, and the like. Oligonucleotides useful in the present invention for identifying the IL marker include those listed below in Sequence ID Nos 1–10 and in the examples.

The method of the present invention therefore provides for identifying diabetic patients expressing a multiple genetic polymorphism pattern for cytokine genes associated with risk of sight-threatening diabetic retinopathy and who would therefore have an increased risk of sight-threatening diabetic retinopathy. Control patterns may be run concurrently. However, it is anticipated that the method may be conducted without concurrent testing of control specimens. From this is determined the number of polymorphisms carried by the diabetic patient that are associated with diabetic retinopathy risk. This allows a determination of the overall risk factor for sight-threatening diabetic retinopathy.

The interleukin-1 (IL-1) gene cluster comprises the three cytokine genes (IL-1A, IL-1B and IL-1RN) that have been physically mapped to a 430 kb fragment of DNA on the long arm of human chromosome 2 [Nicklin el al., 1994]. Applicants have described and characterized polymorphisms in these genes, which are associated with several autoimmune diseases (McDowell et al., 1995; Clay et al., 1994; Cork et al., 1993; Blakemore et al., 1994; Blakemore 1996; Tarlow et al., 1994).

Figure 1:
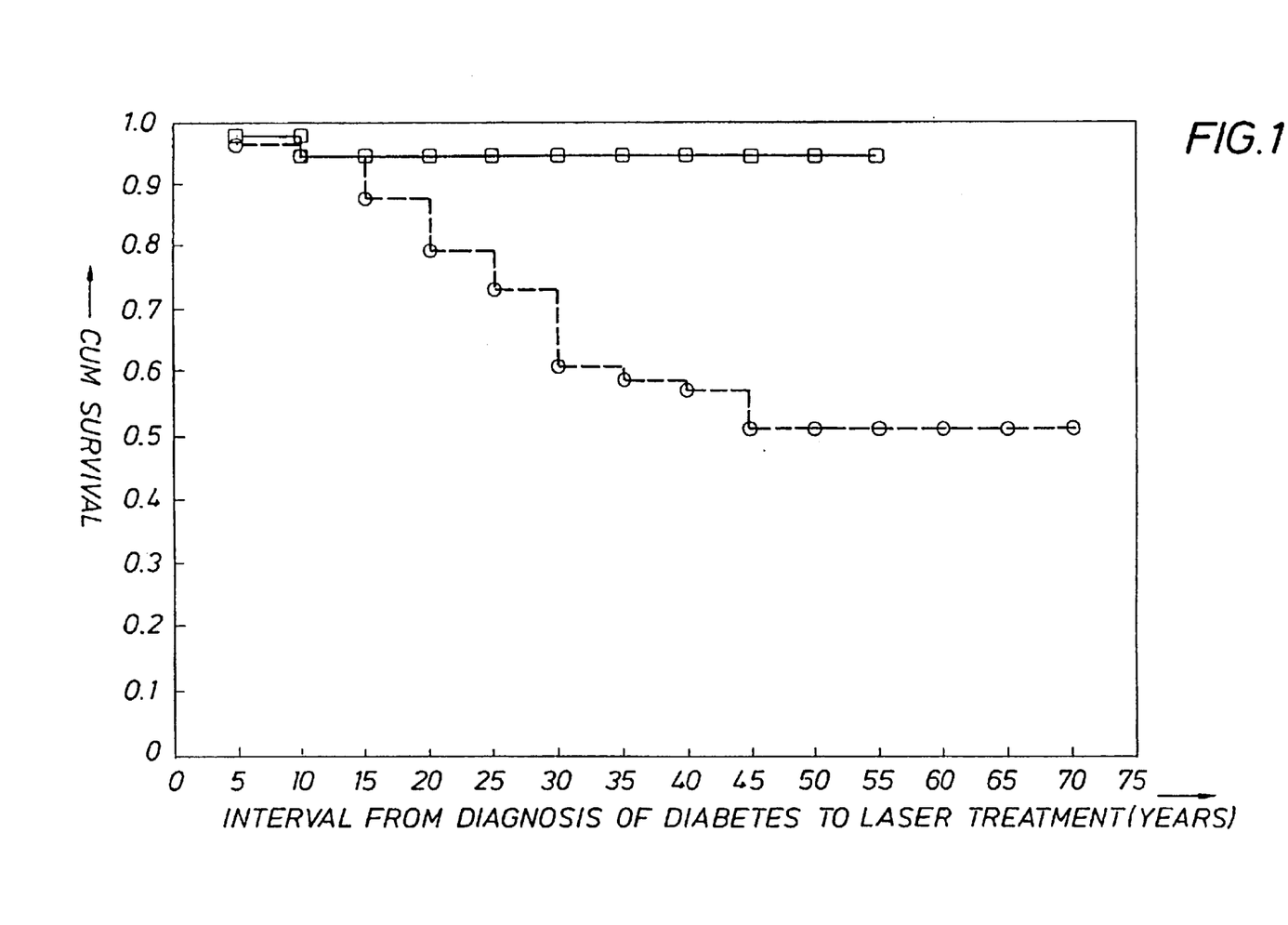
FIG. 1 is a graph of the length of time (survival) between diagnosis of diabetes and onset of proliferative diabetic retinopathy (PDR), as determined by time to first laser treatment for patients with either Type I or Type II diabetes, wherein patients with two copies of IL-1RN allele 2 (□) are compared with those having at most one copy of IL-1RN allele 2 (○)

A specific polymorphism in the gene for IL1ra, one of the molecules that blocks IL-1 activity, appears to protect patients from the development of proliferative diabetic retinopathy (PDR FIG. 1 and Table 1). Patients were screened for the presence of IL-1RN allele 1 or IL-1RN allele 2 and it was found that patients with a genotype of two copies of allele 2 were almost completely protected from PDR.

TABLE 1

PROLIFERATIVE DIABETIC RETINOPATHY

| GENOTYPE | NO PDR | PDR | TOTAL |
|---|---|---|---|
| IL-1RN 2,* OR 1,* | 366 | 93 | 459 |
| IL-1RN 2,2 | 42 | 2 | 44 |
| TOTAL: | 408 | 95 | 503 |

*allele other than 2.
$x^2$: P = 0.008
OR: 5.34
CI: 1.27–22.5
KAPLAN-MEIER p = 0.0227

Figure 2:
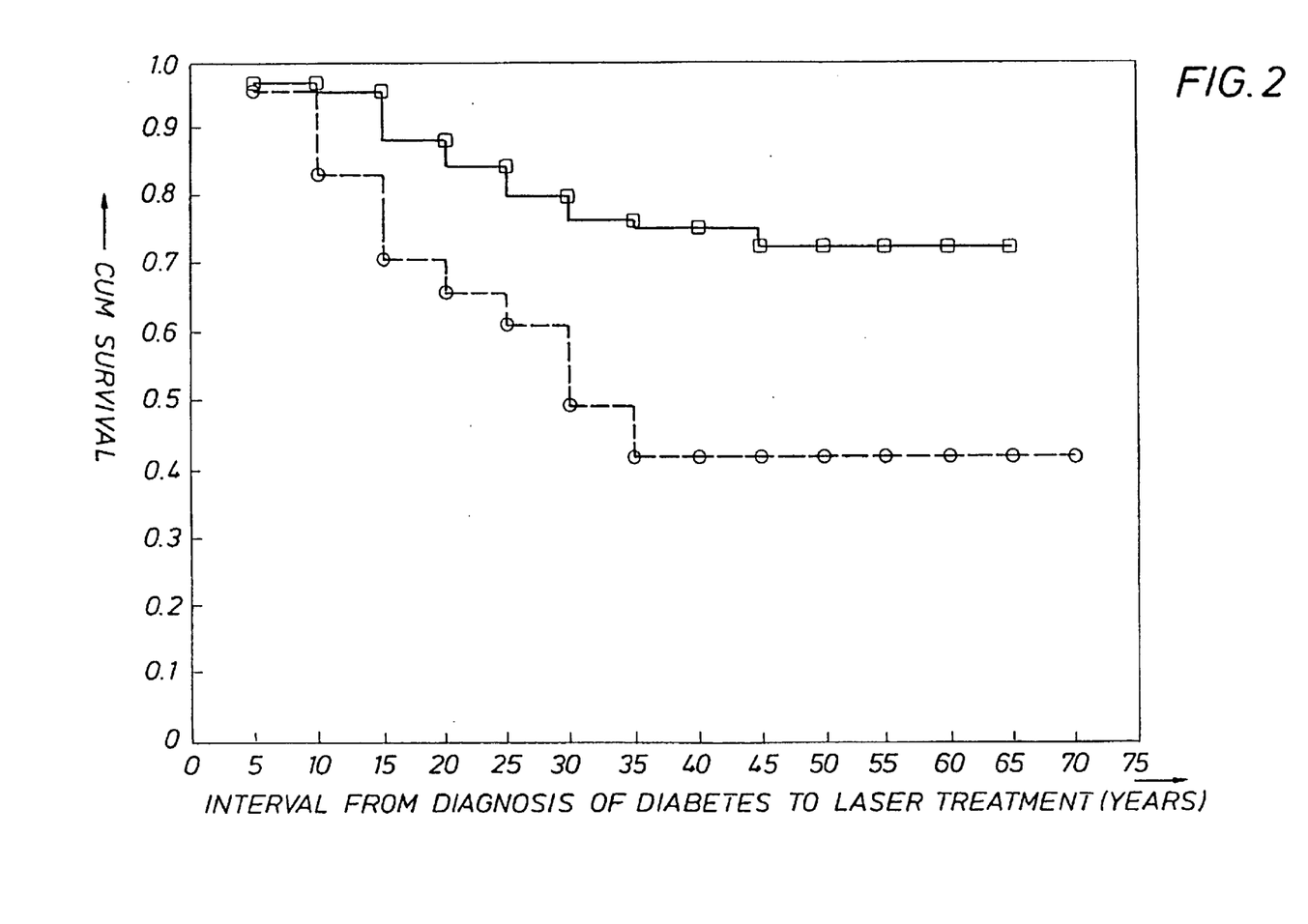
FIG. 2 is a graph of the length of time (survival) between diagnosis of diabetes and onset of diabetic maculopathy, as determined by time to first laser treatment for patients with either Type I or Type II diabetes, wherein patients with a genotype at IL-1A (−889) and IL-1B (−511) have a combined number of copies of rarer alleles (allele 2) of three or more (□) are compared with patients with fewer than three copies (○) of the rarer alleles (allele 2) of IL-1A and IL-1B.

Interestingly, a specific genotype combination of polymorphisms in the genes for IL-1A and IL-1B appears to predispose diabetic patients to the development of maculopathy occurring much earlier in the disease (FIG. 2 and Table 2).

TABLE 2A

MACULOPATHY

| GENOTYPE | NO MAC | MAC | TOTAL |
|---|---|---|---|
| IL-1A + IL-1B Allele 2 < 3 | 389 | 59 | 448 |
| IL-1A + IL-1B Allele 2 ≧ 3 | 30 | 16 | 46 |
| TOTAL: | 419 | 75 | 494 |

$x^2$: P = 0.0001
OR: 3.52
CI: 1.81–6.84
KAPLAN-MEIER p = 0.0017

Each locus has two alleles, allele 1 and allele 2, with allele 2 being the less common (rarer) allele at both loci. Patients were evaluated for their allelic genotype at these loci and patients with three or four copies of allele 2 (at the combined loci) were significantly more susceptible to maculopathy, having an Odds Ratio of 3.52. The genotypes that predispose to maculopathy include:

| IL-1A (−889) + | IL-1B (−511) |
|---|---|
| 1,2 + | 2,2 |
| 2,2 + | 1,2 |
| 2,2 + | 2,2. |

B. IL-1RN 2,2 PATIENTS REMOVED

| GENOTYPE | NO MAC | MAC | TOTAL |
|---|---|---|---|
| IL-1A + IL-1B Allele 2 < 3 | 360 | 55 | 415 |
| IL-1A + IL-1B Allele 2 ≧ 3 | 26 | 16 | 42 |
| TOTAL: | 386 | 71 | 457 |

$x^2$: P = 0.0001
OR: 4.03
CI: 2.0–8.01
KAPLAN-MEIER p = 0.001

Of further interest is the determination that if diabetic patients with the above genotypes are also screened for their IL-1RN genotype and patients having an IL-1RN 2,2 genotype are removed, the odds ratio is increased to 4.0. This supports the role of IL-1RN as a marker for protection against maculopathy.

Oligonucleotide DNA primers that target the specific polymorphic DNA region within the genes of interest are prepared so that in the PCR reaction amplification of the target sequences is achieved. This embodiment has the advantage of requiring only a small amount of blood and avoids the necessity for venipuncture or a tissue biopsy. Alternatively, in another embodiment buccal smears are used. Other means for collecting DNA and determining polymorphism patterns as known in the art can be used.

The primers that were used in the Examples are set forth in SEQ ID Nos: 1–6. Other primers can be used that can be determined as known in the art. For example, the following additional primers can be used:
Primers For IL-1(−889)
  a) 5'-TGT TCTA CCA CCTG AAC TAGG C-3'(−967/−945) (SEQ ID No:7)
    5'-TTA CATA TGA GCCT TCC ATG-3' (−888/−869) (SEQ ID No:8)
  b) 5'-AAG CTT GTT CTA CCA CCT GAA CTA GGC-3' (SEQ ID No:9)
    5'-TTA CAT ATG AGC CTT CCA TG-3' (SEQ ID No:10)

The amplified DNA sequences from the template DNA may then analyzed using restriction enzymes to determine the genetic polymorphisms present in the amplified sequences and thereby provide a genetic polymorphism profile of the patient.

One of the primary components of the inflammatory and other immune responses is cytokine production. Cytokines are peptide/protein immunomodulators that are produced by tissue cells and activated immune cells including thymus-derived T lymphocytes (T-cells), B lymphocytes and monocyte/macrophages. The cytokines include interleukins (IL-1 through IL-17), colony stimulating factors (CSFS) for granulocytes and/or macrophages (CSF-G, CSF-M, CSF-GM), tumor necrosis factors (TNFs α & β), and interferons (IFN α, β & γ). The basic activity of IL-1 includes the combined activities of IL-1α, IL-1β and IL-1 receptor antagonist (IL-1ra). (For a review, see Duff, 1993; and Basic and Clinical Immunology, 8th Ed., 1994, Stites, Terr & Parslow, editors, Chapter 9, pgs. 105–123.). Association of a single cytokine polymorphism and autoimmune disease states have been found as, for example, in Systemic Lupus Erythematosus, Ulcerative Colitis and Juvenile rheumatoid arthritis [Mansfield et al., 1994; Verjans et al., 1992; Blakemore et al., 1994; McGuire et al., 1994; McDowell et al., 1995].

Specific polymorphisms in IL-1A, IL-1B and IL-1RN are associated with increased risk of sight-threatening diabetic retinopathy even though a retinopathy has not traditionally been thought of as an inflammatory condition. The polymorphisms for these genes are as follows:

IL-1A: (Chromosome 2 at 2q12-14)

The alleles of a bi-allelic polymorphism of a single base variation (C/T) at −889 are identified by allele-specific cleavage using a restriction enzyme. The gene is designated IL-1A while the product (cytokine) is designated IL-1α. Allele 1 is C and allele 2 is T at base −889. The full restriction enzyme recognition site is created by introducing a partial site by mutation in the PCR reaction with a modified primer sequence. The site is completed by the sequence of one of the alleles of the polymorphism. After restriction enzyme digestion by NcoI of the products of the PCR reaction, the DNA is separated electrophoretically by size.

From this gel (or a southern blot of it probed with a radioactive internal DNA sequence) the alleles of the polymorphism are identified. The uncut fragment (larger) is the rarer allele (allele 2) in Northern European populations.

IL-1B: (Chromosome 2; 2q12-14)

Two bi-allelic polymorphisms can be typed in two different PCR products using allele-specific cleavage at naturally-occurring sites in the alleles. Allele identification is by size of fragment after restriction digestion and separation in an agarose gel. The gene is designated IL-1B while the product (cytokine) is designated IL-1β. The sites are single base variations (C/T) at −511 (referred to as IL-1B (−511)) and at +3953 (referred to as IL-1B (+3953)) and are identified by allele-specific cleavage using restriction enzymes. For each polymorphism allele 1 is C and allele 2 is T, with allele 2 being the rarer allele.

IL-1RN: (Chromosome 2; 2q12-14)

Five (5) alleles of the intron 2 variable number tandem repeat (VNTR) polymorphism can be typed by electrophoretic sizing by the number of repeats present. PCR is used to amplify the VNTR region by using primers based on the flanking DNA sequences of the VNTR. The gene is designated IL-1RN while the product (cytokine) is designated IL-1ra. Allele 1 contains four repeats and the PCR product is 412 bp; Allele 2 contains two repeats and the PCR product is 240 bp; Allele 3 contains five repeats and is 498 bp; Allele 4 contains three repeats and is 326 bp; and Allele 5 contains six repeats and is 584 bp.

The patient's cytokine polymorphism profile, i.e., the different alleles present at each of the typed loci (genotype), may be compared with control standards to allow identification of the alleles. In one embodiment, controls are provided that are ethnically and gender matched to accommodate genetic variations within subpopulations.

An odds ratio (approximate relative risk) has been derived to test the association between allelic polymorphism pattern (genotype) at these specific loci and development of disease. This provides predictive information that is used in the clinical management.

The above discussion provides a factual basis for a method and for a kit for the identification of a patient's genetic polymorphism pattern associated with increased risk of sight-threatening diabetic retinopathy. The identification of those at risk for severe disease allows preventive measures to be initiated prior to disease onset. Further, those patients who have multiple risk factors, that is risk factors in addition to those determined by the present invention, can be particularly monitored since their risk is extremely high. The methods used with and the utility of the present invention can be shown by the following example.

EXAMPLE

General Methods

Reactions and manipulations involving nucleic acid techniques, unless stated otherwise, were performed as generally described in Sambrook et al., 1989, *Molecular Cloning: A Laboratory Manual*, Cold Spring Harbor Laboratory Press; polymerase chain reaction (PCR) was carried out generally as described in PCR Protocols: *A Guide To Methods And Applications*, Academic Press; San Diego, Calif. (1990) and methodology as generally described in U.S. Pat. 4,666,828; 4,683,202; 4,801,531; 5,192,659 and 5,272,057 and McDowell et al., 1995, these cited references incorporated herein by reference.

Enzymes used in PCR were from GIBCO BRL, thermocyclers were either Perkin-Elmer or Biometra. Restriction enzymes NcoI and TaqI were from Promega (US). Restriction enzymes AvaI and Bsu36I were from NEB (US). Other reagents were from Gibco (UK).

Statistical Analysis $X^2$ analysis was used. Where required the analyses were performed with the SAS statistical package. The Odds Ratio (relative risk) is calculated from a 2×2 contingency table as described by Woolf [1955] as shown below. The following formula: (A×D)/(C×B) is used to calculate the Odds Ratio.

| Sample Contingency Table | | |
| --- | --- | --- |
| Genotype of Interest | Phenotype 1 | Phenotype 2 |
| Present | A | B |
| Absent | C | D |

For each cytokine, the probabilities of (I)having two copies of the rarer polymorphism or (ii) the total number of copies of the rarer polymorphism in the disease groups (i.e. those with PDR and CSME) compared to the control population was determined using a $X^2$ test and calculating the odds ratio.

Multivariate analysis for combinations of cytokine gene polymorphisms was performed using a factorial analysis of variance (ANOVA) for the likelihood of developing PDR or CSME. The interval to the onset of PDR or CSME was determined using Kaplan-Meier univariate analysis for each cytokine and a Cox proportional hazard model (multivariate regression analysis) for interactions between different cytokines and the patients sex and age at diagnosis was constructed. For the Cox regression, a forward stepwise procedure was used on the basis of the likelihood-ratio statistic (probability for entry of 0.05 or less and of 0.10 or more for removal).

Genotyping

Genetic polymorphisms associated with sight-threatening diabetic retinopathy in adults were determined using the protocol of McDowell et al. [1995]. PCR conditions for each polymorphism were performed as previously described [Di Giovine et al., 1992; Tarlow et al., 1994; Pociot et al., 1992] and as detailed herein below. The different alleles were identified on gels, as indicated, and stained with 0.2 μg/ml ethidium bromide and visualized under UV light. Negative controls without DNA were performed in each experiment.

DNA Preparation

DNA was extracted from whole blood using a modification of the salt-out method (Nucleon II™, Scotlab, UK).

PCR Amplification and Product Sizing Protocols for Selected Alleles

The reactions for all the polymorphisms were carried out in 50 μl reactions comprising 10 reaction buffer (final concentration 1mM Tris-HCl, 5 mM KCl 1, dNTPs (final concentration 0.8 mM, Taq polymerase (1.25U) and W-1 detergent (0.05%) The MgCl, and primer concentrations varied for each polymorphism.

IL-1A (−889): The single base variation (C/T) polymorphism at IL-1A base −889 was identified as follows:

SCREENING: PCR amplification of genomic templates. One mismatch inserted in a primer to complete an NcoI site if C is available at −889.

PRIMERS: The following primers were used in the Example and were produced in an ABI DNA synthesizer based on the genomic sequences [Furutani et al., 1986; GENBANK X03833].

5'AAG CTT GTT CTA CCA CCT GAA CTA GGC 3' (−967/−945) (SEQ ID No:1)

5'GTA CCT TCC GAG TAT ACA TT 3' (−888/−869) (SEQ ID No:2)

PCR CONDITIONS:
Primers final concentration of 1.0 μM and 1.5 mM final concentration of MgCl.
1 cycle [96° C. (1 minute)];
35 cycles [94° C. (1 minute), 46° C. (1 minute), 74° C. (1 minute)];
1 cycle [72° C. (5 minutes)].

RESTRICTION ENZYME DIGESTION: Digestion was with 6 Units per 5 μl reaction mixture of NcoI at 37° C., overnight. Sizing was by 6%. PAGE (150V for 2.5 hours)

PREDICTED RESULTS FROM DIGESTION:
Allele 1 (C); NcoI digestion of PCR products of allele 1 will yield 83 and 16 basepair (bp) fragments.
Allele 2 (T) NcoI digestion of PCR products of allele 2 (rarer allele) will be ineffective and yield a 99 basepair (bp) product.

IL-1B (−511): The single base variation (C/T) polymorphism at IL-1B base-(−511) was identified as follows:

SCREENING: PCR amplification of genomic templates. The single base variation completes an AvaI site on allele 1 (C), a Bsu36I site on allele 2 (T).

PRIMERS: The following primers were produced in an ABI DNA synthesizer based on the genomic sequences [Clark et al., 1986; GENBANK X04500].

5'TGG CAT TGA TCT GGT TCA TC 3' (−702/−682) (SEQ ID No:3)

5'GTT TAG GAA TCT TCC CAC TT 3' (−417/−398) (SEQ ID No:4)

PCR CONDITIONS:
Primers final concentration of 1.0 mM and 2.5 mM final concentration of MgCl.
1 cycle [95° C. (2 minutes)];
35 cycles [95° C. (1 minute), 53° C. (1 minute), 74° C. (1 minute)];
1 cycle [74° C. (4 minutes)].

RESTRICTION ENZYME DIGESTION: Digestion was with 3 Units per 30 μl reaction mixture of AvaI and at 37° C., for 8 hours or overnight. Sizing was by electrophoretic mobility (8% PAGE at 150V for 2.5 hours).

PREDICTED RESULTS FROM DIGESTION:
Allele 1 (C) AvaI digestion of PCR products of allele 1 will yield 190 and 114 bp fragments. Bsu36I digestion of PCR products of allele 1 will be ineffective and yield a 304 bp product.
Allele 2 (T) AvaI digestion of PCR products of allele 2 (rarer allele) will be ineffective and yield a 304 bp product. Bsu36I digestion of PCR products of allele 2 will yield 190 and 114 bp fragments.

IL-1RN: Intron 2 of the IL-1RN gene contains a VNTR region and the polymorphism of this region gives rise to five (5) alleles as described herein above which were identified as follows:

SCREENING: PCR amplification of genomic templates followed by assessment of the size of the product after separation on agarose gels.

PRIMERS: The following primers were produced in an ABI DNA synthesizer based on the genomic sequences:

5'CTCAGCAACACTCCTAT 3'(SEQ ID No:5)

5'TCCTGGTCTGCAGGTAA 3'(SEQ ID No:6)

PCR CONDITIONS:
1.75 mM (final concentration) MgCl$_2$ and cycling protocol of 1 cycle at 96° C. for 1 minute;
30 cycles of [94° C. (1 minute), 60° C. (1 minute), 70° C. (1 minute)]; and
1 cycle at 70° C. for 2 minutes.

SIZING
Electrophoresis on 2% agarose gel at 90V for 45 minutes.

PREDICTED RESULTS FROM SIZING:
Allele 1 contains four repeats and is 412 bp;
Allele 2 contains two repeats and is 240 bp;
Allele 3 contains five repeats and is 498 bp;
Allele 4 contains three repeats and is 326 bp; and
Allele 5 contains six repeats and is 584 bp.

Although there are five known alleles at the IL-1RN locus alleles 3, 4 and 5 are rare. The predicted results are based on the assumption that the polymorphisms are and exact multiple of an 86 basepair repeat +68 basepairs as described above. However, as is known in the art, the size may vary slightly due to reading errors and the like. One skilled in the art of would know and compensate for such errors.

Patients

Data is available on 539 patients with diabetes who attended the Diabetic clinic and were enrolled into the study (Table 3). After informed consent was received, a sample of blood was obtained and the polymorphisms for cytokine genes IL-1A (−889), IL-1B (−511) and IL-1RN were determined as described.

TABLE 3

Mean Age At Diagnosis or Diabetes

| | M + F | M | F |
|---|---|---|---|
| Combined Type I + Type II | | | |
| CONTROLS | 24.4 | 24.7 | 24.5 |
| CSME | 36.3 | 35.3 | 37.3 |
| PDR | 27.6 | 27.9 | 27.1 |
| Type I Only | | | |
| CONTROLS | 23.0 | 23.5 | 22.5 |
| CSME | 24.0 | 25.4 | 20.9 |
| PDR | 18.1 | 19.6 | 14.9 |
| Type II Only | | | |
| CONTROLS | 51.9 | 49.8 | 56.5 |
| CSME | 49.5 | 50.8 | 48.2 |
| PDR | 50.2 | 51.2 | 48.2 |

Of the patients in the study, 166 stated that they had received laser treatment for retinopathy, of which ten were found not to have had laser treatment and case-notes were not available on nine. The number of patients who denied laser treatment but who had, (i.e. false negatives) could not be determined. The remaining 383 served as a control population of diabetics.

Data Collected

The case-notes from the diabetic clinic were reviewed to obtain:

The date of birth and sex of the patient, the date of diagnosis of diabetes and age at diagnosis, if they had Type I or Type II diabetes and the presence of nephropathy or neuropathy.

The case-notes from visits to the Ophthalmology Clinic were reviewed and at each attendance the following details were obtained to record:

Date of attendance, interval from diagnosis of diabetes, Snellen visual acuity, presence of background retinopathy, pre-proliferative, proliferative and advanced diabetic retinopathy, and the presence of vitreous hemorrhage. The PDR was noted as NVD, NVE or both. The presence of maculopathy was noted and recorded as focal, diffuse, ischemic or mixed.

Results

Changes in the frequencies of cytokine gene polymorphisms are associated with proliferative diabetic retinopathy (PDR) and maculopathy. The interval from diagnosis of diabetes to the onset of sight-threatening retinopathy was associated with specific cytokine polymorphisms, either singly or in combination.

All patients were analyzed together, then according to the type of diabetes. Overall, 77 patients in the study developed maculopathy, 46 males and 31 females. Of the 77 who developed maculopathy, 40 were Type I diabetics who developed maculopathy and 37 were Type II diabetics. Overall 96 diabetic patients developed PDR, 69 with Type I diabetes and 27 with Type II diabetes. Average age at diagnosis of diabetes is set forth in Table 3. There was a mean of 220.9 months follow-up (range 0–1065 months) for each patient with no significant differences between the sexes in length of follow up.

Clinically-significant Macular Oedema (CSME)

The mean interval to the onset of maculopathy was 166 months (0–840 m), 224 m (0–516 m) for Type I and 110.1 m (1–291 m) for Type II diabetics.

Genotypes were analyzed for relationship to the survival time from diagnosis of diabetes to treatment for proliferative diabetic retinopathy, with the following findings. Few diabetics with two copies of allele 2 at the IL-1RN locus developed PDR even 50 years after diagnosis of diabetes. However, up to 50% of the diabetics with one or no copies of allele 2 developed PDR as shown in FIG. 1 and Table 1 (above)

Genotypes were analyzed for relationship to the survival time from diagnosis of diabetes to treatment for maculopathy, with the following findings. Diabetics with at least three copies of the less frequent allele (allele 2) at the combined loci for IL-1A (−889 locus) and IL-1B (−511 locus) showed significantly more and earlier maculopathy than individuals with less than three copies of allele 2 as shown in FIG. 2 and Table 2A (Odds Ratio 3.52). Removing patients who had an IL-1RN 2,2 genotype increased the Odds Ratio to 4.0 (Table 2B) (above).

The present invention therefore provides a method of identifying diabetic patients at risk for sight-threatening retinopathy to allow early treatment.

Throughout this application various publications and patents are referenced. Full citations for the referenced publications and patents not included herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 3

References

Adamis et al., "Increased vascular endothelial growth factor levels in the vitreous of eyes with proliferative diabetic retinopathy" *Am. J. Opthalmol.*, 118(4):445–50 (Oct. 15, 1994).

Aiello et al., "Vascular endothelial growth factor in ocular fluid of patients with diabetic retinopathy and other disorder©s" *NEJM*, 331:(22):1480–7 (Dec. 1, 1994).

Basic and Clinical Immunology, 8th Ed. eds Stites, Terr & Parslow, Chapter 9, pgs 105–123.

Blakemore et al., "Interleukin-1 receptor antagonist gene polymorphism as a severity factor in systemic lupus erythematosus" *Arthritis and Rheumatism* 37(9): 1380–1385 (1994).

Blakemore et al., "Interleukin-1 receptor antagonist allele (IL1RN*2) associated with nephropathy in diabetes mellitus" *Human Genetics* 97:369–374 (1996).

The Center for Disease Control and Prevention: "National Diabetes Fact sheet" Nov. 3, 1995.

Clark et al., "Genomic sequence for human prointerleukin 1 beta: possible evolution from a reverse transcribed prointerleukin 1 alpha gene" *Nucl Acids Res* 14:7897–7914 (1986) [published erratum appears in *Nucleic Acids Res* 15(2):868 (1987).

Clay et al., "Interleukin-1 receptor antagonist gene polymorphism association with lichen sclerosis" *Human Genetics*, 94:407 (1994).

Cork et al., "Psoriasis and interleukin-1. A translation." *Journal of the Royal College of Physicians of London*, 27:366 (Abstract) (1993).

de Giovine et al., "Single base polymorphism at −511 in the human interleukin-1β gene (IL10)" *Human Molecular Genetics* 1, No. 6:450 (1992).

Dinarello, "Interleukin-1 and Interleukin-1 antagonism" *Blood*, 77:1627 (1991).

DRS Report No. 7, "A modification of the Airlee House classification of diabetic retinopathy" The Diabetic Retinopathy Research Group, *Invest. Ophthmol. Vis. Sci.*, 21:210–26 (1981).

DRS Report Number 8, "Photocoagulation treatment of proliferative diabetic retinopathy. Clinical application of diabetic retinopathy study (DRS) findings" (1981)

Duff, "Cytokines and anti-cytokines" Br. J. Rheumatol 32 (Suppl 1):15–20 (1993).

ETDRS Number 1, "Photocoagulaion for diabetic macular edema" Early Treatment Diabetic Retinopathy Study Research Group, *Arch Ophthalmol* 103:1796–1806 (1985).

ETDRS No. 9, "Early photocoagulation for diabetic retinopathy" Early Treatment Diabetic Retinopathy Study Research Group, *Ophthalmolog*, 98:766–785 (1991).

ETDRS Number 12, "Fundus photographic risk factors for progression of diabetic retinopathy Early Treatment Diabetic Retinopathy Study Research Group, *Ophthalmology* 98:823–833 (1991).

Franks, et al., "Cytokines in human intraocular inflammation" *Current Eye Research* 11 (suppl): 187–91 (1992).

Furutani et al., "Complete nucleotide sequence of the gene for human interleukin 1 alpha" *Nucl Acids Res* 14:3167–3179 (1986).

Hu et al., "Inhibition of angiogenesis in rats by IL-1 receptor antagonist and selected cytokine antibodies" *Inflammation* 18(1):45–58 (1994).

Hu and Fan, "Protein kinase C inhibitor calphostin C prevents cytokine-induced angiogenesis in the rat" *Inflammation* 19(1):39–54 (1995).

Klein et al., "The Wisconsin Epidemiologic Study of diabetic retinopathy XIV. Ten-year incidence and progression of diabetic retinopathy [see comments]. Department of Ophthalmology and Visual Sciences, University of Wisconsin Medical school, Madison. Arch Ophthalmol 112(9):1217–1228 (1994).

Ko, et al., "An (A–C), Dinucleotide Repeat Polymorphic Marker at the 5' End of the Aldose Reductase Gene Is Associated With Early-Onset Diabetic Retinopathy in NIDDM Patients" *Diabetes* 44:727–732 (1995).

Koyama et al., "Migratory and proliferative effect of platelet-derived growth factor in rabbit retinal endothelial cells: evidence of an autocrine pathway of platelet-derived growth factor" *J. Cell Physiol.*, 158(1):1–6 (Jan. 1994).

Lowe et al., "Regulation of growth factor MRNA levels in the eyes of diabetic rats" *Metabolism*, 44(8):1038 (1995).

Malecaze et al., "Detection of vascular endothelial growth factor messenger RNA and vascular endothelial growth factor-like activity in proliferative diabetic retinopathy. Arch. Ophthalmol., 112(11): 1476–82 (Nov. 1994).

Mansfield et al., "Novel genetic association between ulcerative colitis and the anti-inflammatory cytokine interleukin 1 receptor antagonist" Gastroenterology 106:637–642 (1994).

McDowell et al., "A genetic association between juvenile rheumatoid arthritis and a novel interleukin-1 alpha polymorphism" Arthritis & Rheumatism 38-221–228 (1995).

Mandrup-Poulsen et al., "Involvement of interleukin-1 and interleukin-1 antagonist in pancreatic β-cell destruction in insulin-dependent diabetes mellitus" Cytokine, 5:185–191 (1993).

McGuire et al., "Variation in the TNF-α promoter region associated with susceptibility to cerebral malarial" *Nature* 371:508–511 (1994). Michelson, 1940 [need citation]

Murata et al., "Vascular endothelial growth factor plays a role in hyperpermeability of diabetic retinal vessels" *Ophthalmic Res.*, 27(1):48–52 (1995).

Nedospasov et al., "Tandem arrangement of genes coding for TNF∂ and lymphotoxin (TNFβ) in the human genome" *Cold Spring Harbor Symp Quant Biol* 60:611–624 (1986).

Nicklin et al., "A physical map of the region encompassing the human interleukin-1β, and interleukin-1 receptor antagonist genes" *Genomics*, 19:382.9 (1994).

Pe'er et al., "Hypoxia-induced expression vascular endothelial growth factor by retinal cells is a common factor in neovascularizing ocular diseases" Lab. Invest., 72(6) 638–45 (June, 1995).

Pfeiffer, "Vascular endothelial growth factor in the aqueous humor in diabetic retinopathy and other diseases of the retina" Dtsch Med Wochenschr, 120(42):1453 (Oct. 20, 1995).

Pfeiffer and Schatz, "Diabetic microvascular complications and growth factors" *Exp. Clin. Endocrinol.* Diabetes, 103(1):7–14 (1995).

Pociot et al., "A TaqI polymorphism in the human interleukin-1β (IL-1β) gene correlates with IL-1β secretion in vitro" *Eur. J. Clin. Invest.*, 22:396–402 (1992).

Seaquist et al., "Familial clustering of diabetic kidney disease. Evidence for genetic susceptibility to diabetic nephropathy" *NEJM*, 320:1161 (1989).

McGuire et al.: "Variation in the TNF-α promoter region associated with susceptibility to cerebral malarial, *Nature* 371:508–511 (1994).

Tarlow et al., "Severity of Alopecia Areata is associated with a polymorphism in the interleukin-1 receptor antagonist gene" *Journal of Investigative Dermatology*, 103:287 (1994).

Todd, "Genetic control of auto immunity in Type 1 diabetes" *Immunology Today*, 11:122 (1990).

Verjans et al., "Polymorphism of the tumor necrosis factor region in relation to disease: An overview" *Rheum Dis Clin North Am* 18:177–186 (1992).

Woolf, B., "Estimating the relationship between blood groups and disease" *Annals of Human Genetics* 19:251–253 (1955).

---

We claim:

1. A method of predicting increased risk of sight-threatening diabetic retinopathy, comprising identifying in isolated genomic DNA from a sample previously taken from a diabetic patient a genetic polymorphism pattern comprising a polymorphism selected from the group consisting of: IL-1RN (VNTR) allele 1, IL-1 A (−511) allele 2, and IL-1B (−889) allele 2, wherein the presence of the genetic polymorphism pattern is predictive of an increased risk of sight-threatening diabetic retinopathy.

2. A method according to claim 1, wherein said step for identifying in the DNA a genetic polymorphism pattern for IL-1A, IL-1B and IL-1RN comprises amplification of target DNA sequences with a polymerase chain reaction (PCR) and at least one PCR primer, wherein the PCR primer is selected from the group consisting of:

5'AAG CTT GTT CTA CCA CCT GAA CTA GGC 3' (SEQ ID NO; 1);
    5'GTA CCT TCC GAG TAT ACA TT 3' (SEQ ID NO: 2);
    5'TGG CAT TGA TCT GGT TCA TC 3' (SEQ ID NO: 3);
    5'GTT TAG GAA TCT TCC CAC TT 3' (SEQ ID NO: 4);

5'CTCAGCAACACTCCTAT 3' (SEQ ID NO: 5);
5'TCCTGGTCTGCAGGTAA 3' (SEQ ID NO: 6);
5'TGTTCTACCACCTGAACTAGGC 3' (SEQ ID NO: 7);
5'TTACATATGAGCCTTCCATG 3' (SEQ ID NO: 8);
5'AAGCTTGTTCTACCACCTGAACTAGGC 3' (SEQ ID NO: 9); and
5'TTACATATGAGCCTTCCATG 3' (SEQ ID NO. 10).

3. A method according to claim 2, wherein said step for identifying in the DNA a genetic polymorphism pattern for genes IL-1A, IL-1B and IL-1RN comprises restriction enzyme digestion with restriction enzymes NcoI, AvaI, and Bsu36I.

4. A method according to claim 2, wherein the genetic polymorphism pattern is selected from the group consisting of
 (a) IL-1A(−889)2,2 and IL-1B(−511)2,2;
 (b) IL-1A(−889)1,2 and IL-1B(−511)2,2; and
 (c) IL-1A(−889)2,2 and IL-1B(−511)1,2.

5. A method according to claim 2 wherein the genetic polymorphism pattern is selected from the group consisting of
 (a) IL-1A(−889)2,2 and IL-1B(−511)2,2;
 (b) IL-1A(−889)1,2 and IL-1B(−511)2,2; and
 (c) IL-1A(−889)2,2 and IL-1B(−511)1,2.

* * * * *

UNITED STATES PATENT AND TRADEMARK OFFICE
CERTIFICATE OF CORRECTION

PATENT NO. : 6,713,253 B1
DATED : March 30, 2004
INVENTOR(S) : Gordon W. Duff, Patrick R. S. Richardson and Ian G. Rennie It is certified that error appears in the above-identified patent and that said Letters Patent is hereby corrected as shown below:

Column 21,
Line 63, replace "(-511)" with -- (-889) --.
Line 64, replace "(-889)" with -- (-511) --.

Column 23,
Line 14, replace "Bsu361" with -- Bsu36I --.

Column 24,
Line 1, replace "2" with -- 1 --.

Signed and Sealed this

Nineteenth Day of April, 2005

JON W. DUDAS
*Director of the United States Patent and Trademark Office*